United States Patent [19]

Reichenberger et al.

[11] Patent Number: 4,879,993

[45] Date of Patent: Nov. 14, 1989

[54] SHOCK WAVE SOURCE FOR GENERATING A SHORT INITIAL PRESSURE PULSE

[75] Inventors: Helmut Reichenberger, Eckental; Rudolf Schittenhelm, Erlangen, both of Fed. Rep. of Germany

[73] Assignee: Siemens Aktiengesellschaft, Berlin and Munich, Fed. Rep. of Germany

[21] Appl. No.: 105,004

[22] Filed: Oct. 6, 1987

[30] Foreign Application Priority Data

Oct. 29, 1986 [DE] Fed. Rep. of Germany ....... 3636834

[51] Int. Cl.[4] ............................................ A61B 17/22

[52] U.S. Cl. ................................ 128/24 A; 128/328; 128/660.03

[58] Field of Search ................ 128/24 A, 328, 660.03; 367/175

[56] References Cited

U.S. PATENT DOCUMENTS

| | | | |
|---|---|---|---|
| 4,617,931 | 10/1986 | Dory | 128/328 |
| 4,660,186 | 4/1987 | Massa | 367/175 |
| 4,669,472 | 6/1987 | Eisenmenger | 128/328 |
| 4,697,579 | 10/1987 | Wessels et al. | 128/328 |
| 4,766,888 | 8/1988 | Oppelt | 128/24 A |
| 4,793,329 | 12/1988 | Mahler et al. | 128/24 A |
| 4,794,914 | 1/1989 | Mahler et al. | 128/24 A |

FOREIGN PATENT DOCUMENTS

| | | | |
|---|---|---|---|
| 3312014 | 10/1984 | Fed. Rep. of Germany | 128/328 |
| 3502751 | 7/1986 | Fed. Rep. of Germany | 128/328 |
| 8322427 | 7/1987 | Fed. Rep. of Germany | 128/328 |

*Primary Examiner*—Ruth S. Smith
*Assistant Examiner*—John D. Zele
*Attorney, Agent, or Firm*—Hill, Van Santen, Steadman & Simpson

[57] ABSTRACT

A shock wave source has a coil carrier, a planar or concave coil, a membrane consisting of electrically conductive material and a foil consisting of electrically non-conductive material. The membrane is disposed between the coil and the foil so as to be held tightly therebetween but having a perimeter which is capable of substantially unrestrained movement. Upon the application of a high voltage pulse to the coil, the resulting field causes the membrane to be rapidly repelled, however, only the mechanical forces of the membrane act on the foil, with no electromagnetic forces generated by the coil acting on the foil. The resulting pressure pulse is intensified to form a shock wave pulse in a transmission medium adjacent to the foil. The substantially unrestrained perimeter of the membrane disposed between the coil and the foil permits an initial pressure pulse of short duration to be generated, which provides the further advantages of a short approach path, a small focus zone, a high focusing factor, low electrical and thermal stress on the shock wave source and a low acoustic energy output into the body of a patient receiving treatment using the shock wave source.

20 Claims, 2 Drawing Sheets

SHOCK WAVE SOURCE FOR GENERATING A SHORT INITIAL PRESSURE PULSE

BACKGROUND OF THE INVENTION

1. Field of the Invention

The present invention is directed to a shock wave source of the type having an electromagnetic coil which is supplied with a high voltage pulse so as to rapidly repel an electrically conductive membrane disposed adjacent to the coil for generating a pressure pulse.

2. Description of the Prior Art

A shock wave source, or shock wave tube, of this type is described, for example, in German OS No. 35 02 751. The use of such a shock wave source in medical technology for disintegrating calculi disposed in the body of a patient is described, for example, in German OS No. 33 12 014. As a result of the high pressure pulse of, for example, 100 bar generated by such a shock wave source, the components of the shock wave source are highly stressed given repeated discharges and shock wave emissions. In particular, the membrane is exposed to strong electromagnetic and mechanical forces, which can lead to a premature material fatigue. In conventional shock wave sources, this membrane is compact and consists of material having high electrical conductivity and high mechanical strength. The membrane is clamped firmly at its edge around the entire perimeter thereof, as described in German OS No. 35 02 751. The membrane is preferably homogeneous, and may consist of a metal such as, for example, copper or an alloy having high conductivity such as bronze or silver-bronze. The membrane may alternatively consist of a carrier, for example, beryllium bronze, or a polymer having an applied coating such as, for example, a galvanic layer of silver or copper.

The duration of the initial acoustic pressure pulse generated by shock wave sources of this type is significant for various reasons. In theory, a shortening of the duration of this initial pressure pulse would result in a shortening of the approach path leading to the formation of a shock wave, a smaller focus zone (−6 dB zone), a higher focusing factor, i.e., a higher peak pressure at the focus given a prescribed initial pressure, lower electrical and thermal stresses on the shock wave source for achieving a defined peak pressure, a relatively slight quantity of acoustic energy output into the body of the patient, and a change in the predominantly effective mechanism of calculus destruction toward an "erosion" of the calculus instead of a "disintegration" as occurs in the case of a relatively long initial pressure pulse. Thus shortening the duration of the initial acoustic pulse provides a number of significant advantages in comparison with conventional techniques.

The duration of the initial pressure pulse is determined primarily by the duration of the discharge current of a capacitor which is connected to the coil, and thus by the electrical properties of the discharge circuit. Another factor contributing to the duration of the initial pressure pulse is the mass of the electrically conductive membrane. If, using a metallic membrane, the impedance of the discharge circuit is reduced by using a capacitor having a smaller capacitance (for example, 0.25 μF instead of 1 μF), the duration of the discharge current will be noticeably shorter but the membrane can no longer completely execute the necessary movement based on the current curve due to its inertia. A pressure pulse having a longer duration and a lower amplitude than in the ideal case results. Using a coated membrane, by contrast, the electrically conductive layer, having a thickness of about 30 through 50 μm is not strong enough to permit the eddy currents induced by the coil to reach full strength, thus also resulting in a reduced efficiency. Practical manufacturing problems do not permit simply using a thicker galvanic layer having the same conductivity as the compact metal layer because joining techniques other than electroplating would be necessary, and such other joining techniques cannot accept the same degree of mechanical loading as an electroplated layer. In general, therefore, efforts to improve the electrical operation of the membrane cause mechanical disadvantages, and vice versa.

SUMMARY OF THE INVENTION

The invention is based on the perceptionof that the aforementioned competing nature of the electrical and mechanical properties of the membrane can be avoided by providing separate membrane components, one of which performs the electrical function of a conventional membrane and the other of which performs the mechanical function.

It is therefore an object of the present invention to provide a shock wave source of the type described above which is capable of producing a short duration initial pressure pulse while avoiding the disadvantages attendant thereto existing in the prior art.

The above object is achieved in accordance with the principles of the present invention by disposing the membrane tightly between the coil and a foil consisting of material of poor electrical conductivity, with the perimeter of the membrane being substantially mechanically unrestrained.

The membrane is a layer, such as a sheet or a disk, having good electrical conductivity.

When a current pulse flows through the coil, the membrane is repelled away from the coil due to the resultant induction, however substantially no radial forces are generated within the membrane, due to the unrestrained perimeter, which would otherwise cause the membrane to wear. The foil is mechanically deflected only by the membrane, but is not acted upon by electromagnetic forces because no current is induced in the foil. The largest mechanical stress of the foil thus occurs at its edge, however, as a consequence of the flexibility and elasticity of the foil, this stress can be accomodated without damage. If necessary, the foil may be reinforced at its edge.

A membrane of aluminum is preferred for good results in obtaining a short duration pressure pulse and a high efficiency. Aluminum has approximately 30% of the mass of a copper or bronze membrane of the same thickness, and has approximately 60% of the conductivity of silver. A preferred embodiment of the invention uses a membrane which uniformly consists of pure aluminum.

Moreover, the duration of the initial pulse can be varied relatively easily by simply interchanging the membrane with a membrane of a differing composition or dimensions.

DESCRIPTION OF THE PREFERRED EMBODIMENTS

Figure 1:
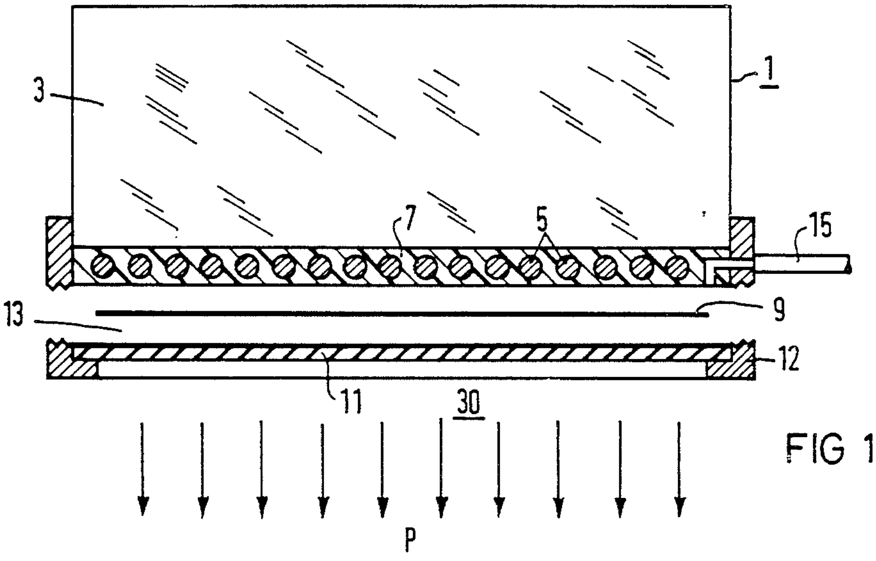
FIG. 1 is a side sectional view, partly exploded, of a shock wave source constructed in accordance with the principles of the present invention using a planar coil.

As shown in FIG. 1, a shock wave source 1 constructed in accordance with the principles of the present invention has a coil carrier 3 having an end face at which a flat coil 5 is attached. The coil 5, for example, may be potted in insulating casting resin 7, and subsequently ground flat at its end face. The windings of the coil 5 are helical.

A membrane 9 is disposed in front of the flat coil 5, with the perimeter of the membrane being substantially mechanically unrestrained. The membrane 9 preferably consists of a metal having low mass and high electrical conductivity such as, for example, aluminum. The membrane 9 preferably has a thickness between about 50 and about 500 μm. The diameter is selected such that movement of the membrane 9 is not significantly influenced at its perimeter by components of the shock wave tube housing. A foil 11, consisting of a material having poor electrical conductivity, is disposed following the membrane 9 in the propagation direction of the shock waves P. The foil 11 is preferably held in place by clamping at its perimeter. The foil 11 preferably consists of polymeric plastic, such as polyimide or polyethylene, which has a certain elasticity. The foil 11 preferably has a thickness of up to about 200 μm. The diameter of the membrane 9 is smaller than the diameter of the foil 11, and is also smaller than the diameter of the mount 12, which clamps or otherwise retains the foil 11 at its perimeter.

The components 5, 9 and 11 are shown in an exploded view in FIG. 1. In the assembled unit, the mount 12 holds the membrane 9 tightly between the coil 5 (i.e., the resin 7) and the foil 11, but without restraining the membrane 9 at its perimeter. A closed volume 13 in which the membrane 9 is disposed is formed when the elements of the mount 12 are fastened together. The membrane 9 is tightly held in this volume 13 in the direction of propagation of the shock waves P, but is radially loosely constrained within this volume.

A feed conduit 15 leads from the exterior of the shock wave source 1 into the volume 13 for cresting an underpressure in the volume 13.

In the embodiment of FIG. 1, the feed conduit 15 proceeds through the casting resin 7 to the exterior of the shock wave source 1.

Figure 2:
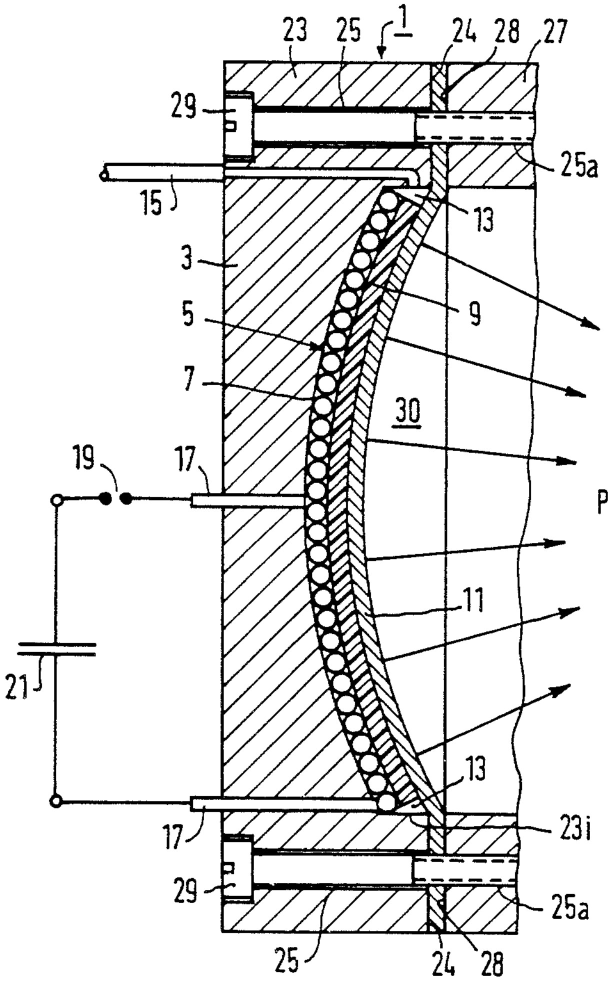
FIG. 2 is a side sectional view of a shock wave source constructed in accordance with the principles of the present invention using a concave coil.

Another embodiment of a shock wave source 1 constructed in accordance with the principles of the present invention is shown in FIG. 2, wherein components corresponding to those already identified in connection with FIG. 1 have the same reference symbols. In this embodiment, the coil carrier 3 is cylindrical and has one face which is concave. A single-layer coil 5 is disposed on the concave face, the coil 5 again being cast in insulating casting resin 7. The coil 5 is connected to a capacitor 21 via a spark gap 19 by an electrical line 17. When the capacitor 21 is charged sufficiently that a spark is generated across the gap 19, the coil 5 will be briefly energized and repel the electrical conductive membrane 9 to generate a pressure pulse.

The coil carrier 3 is part of a first housing component 23 having a plurality of bores 25 at the periphery thereof.

A metallic membrane 9 having the same properties as described in connection with FIG. 1 is disposed in front of the coil 5. The membrane 9 is also curved so as to conform to the shape of coil 5. A flexible non-metallic foil 11 is disposed over the membrane 9, also having properties the same as those described in FIG. 1. The foil 11 is of a size sufficient to extend over a planar surface 24 of the first housing component 23. Again, the membrane 9 is disposed between the coil 5 and the foil 11 so as to be relatively tightly held in the direction of shock wave propagation, but with its perimeter being substantially mechanically unrestrained, so that it is radially loosely constrained. This affords the same separation of electrical and mechanical functions as is achieved in the embodiment of FIG. 1.

A second annular housing component 27 is disposed opposite the first housing component 23. The second housing component 27 has a planar surface 28, with the outer portion of the foil 11 being held between this planar surface and the planar surface 24 of the first housing component 23. The second housing component 27 has bores 25*a* disposed in registry with the bores 25 of the first housing component 23. The bores 25*a* are threaded so that screws or bolts 29 draw the second housing component 27 tightly against the first housing component 23, thus firmly clamping the foil 11 at its outer portion.

Again, the membrane 9 is disposed in a closed volume 13 formed by the casting resin 7, the foil 11, and an interior surface 23*a* of the first housing component 23. A feed conduit 15 which can be connected to a vacuum pump communicates with the volume 13, either through the surface 23*i*, as shown, or through the insulating resin 7 as in FIG. 1.

In both of the embodiments of FIGS. 1 and 2, the volume 13 is evacuated, so that the coil 5, the membrane 9 and the foil 11 are disposed tightly against each other in the direction of shock wave propagation. This is the starting condition before a shock wave P is triggered. For triggering the shock wave P, the membrane 9 is rapidly accelerated away from the coil 5 due to the discharge current of the capacitor 21. Because the membrane 9 is not clamped at its perimeter, substantially no radial forces, which would cause wearing of the membrane 9, act on the membrane 9. The foil 11 is deflected only due to mechanical contact with the membrane 9, but not due to electromagnetic forces. The greatest stress on the foil 11 occurs at its outer region, and can be accomodated without serious damage due to the flexibility and elasticity of the foil 11. After the shock wave P is triggered, the membrane 9 and the foil 11 are pulled back into the described initial position by the vacuum generated in the volume 13.

By using a membrane 9 consisting of aluminum, a very good electrical conductivity and a low weight of the membrane 9 are achieved. In comparison to a membrane 9 consisting of silver or of a bronze alloy, a shorter duration initial acoustic pulse is generated as a result of the different masses (given conditions for the shock wave source 1 which are otherwise identical). This shortening of the pulse duration results in the earlier described advantages of a shorter approach path (given a planar shock wave source with an acoustic lens) leading to the formation of a shock wave, a smaller focus zone, a higher focusing factor, lower electrical and thermal stress on the shock wave source 1, a reduction in the acoustic energy output into the patient's body, and a change in the destruction mechanism of a calculus from "disintegrating" or "shattering" to "erosion" meaning that the size of the calculus is gradually made smaller by the action of the shock waves, as opposed to an immediate break-up of the calculus into smaller pieces. In addition to these advantages, which are directly connected to the shortening of the initial pulse, replacement or changing of the coil 5 or the membrane 9 for varying the properties of the generated shock waves can be easily accomodated. This is accomplished simply by dismantling the housing of the coil carrier 3 from the rear, without the entire shock wave source 1 having to be dismantled. Normally the approach path volume 30 will be water-filled so as to promote shock wave transmission, and because the shock wave source 1 can be dismantled from the rear, this volume does not have to be emptied in order to change the coil 5 or the membrane 9. If clinically necessary, however, a longer initial pressure pulse having a correspondingly longer focus zone and more acoustic energy can be generated using this shock wave source 1. This can be achieved by changing the capacitor 21 from a value of, for example, 0.25 μF for short pulse duration to a capacitance of, for example, 1.0 μF for a longer pulse duration.

Figure 3:
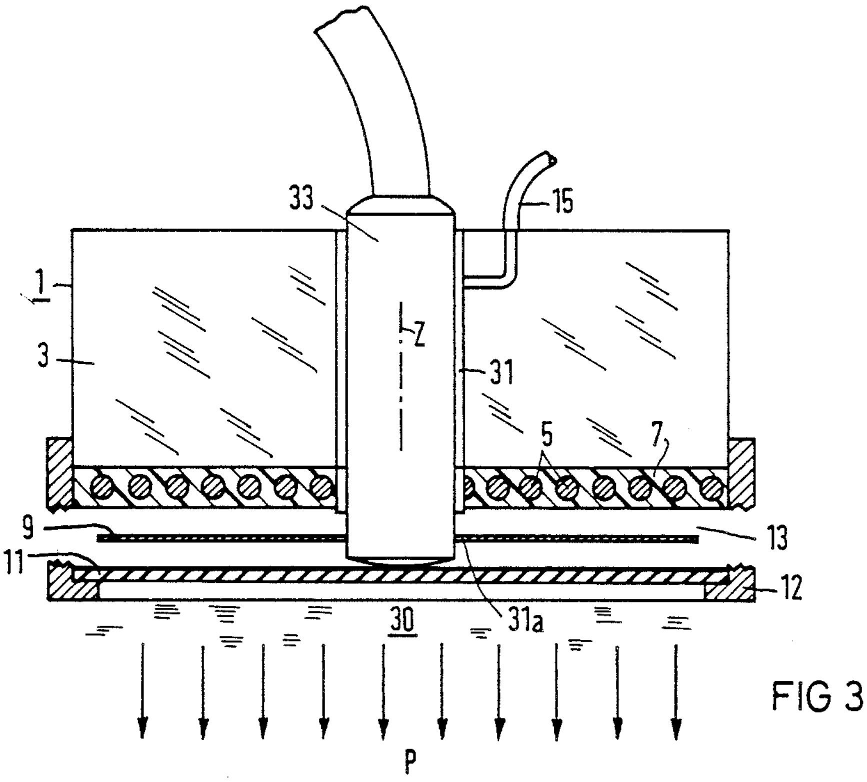
FIG. 3 is a side sectional view, partly exploded, of a further embodiment of a shock wave source constructed in accordance with the principles of the present invention embodying an ultrasound locating means.

A further embodiment of the shock wave source 1 is shown in FIG. 3 wherein the coil carrier 3 and the casting resin 7 has a central recess 31 therein, and the membrane 9 has a central recess 31*a* in registry therewith. A transmission/reception head 33 of an ultrasound locating device is disposed within the recesses 31 and 31*a*. The transmission/reception head 33 is used for identifying the location of a calculus within a patient with respect to the center axis Z of the unit, for example, by a sector scan. In this embodiment the feed conduit 15 communicates with the recess 31.

Even if an ultrasound locating device is not used, it has been found useful to provide the membrane 9 with a central, preferably circular, recess 31*a* (the recess 31 not being present). Experiments have shown that voltage arcing between the coil 5 and the membrane 9 are considerably reduced when the membrane 9 is provided with a central recess 31*a* having a diameter which is about 10% to about 30% of the diameter of the membrane 9. Such a central recess 31*a* in the membrane 9 has also proven advantageous in combination with a concave coil such as shown in FIG. 2. This also permits, in combination with their flexibility, the membrane 9 and the foil 11 to be especially well-matched to the profile of the coil 5 and the insulating casting resin 7.

The foil 11 may be reinforced at the outer portion thereof at which it is clamped, in comparison to its central region, so as to contribute to an extended useful life.

Although further modifications and changes may be suggested by those skilled in the art it is the intention of the inventors to embody within the patent warranted hereon all changes and modifications as reasonably and properly come within the scope of their contribution to the art.

We claim as our invention:

1. A shock wave source comprising:

a high voltage pulse supply;

an electrically conductive coil unit and connection means adapted for connecting said coil unit to said high-voltage pulse supply;

a flexible foil consisting of material having poor electrical conductivity;

means in contact with the periphery of said coil for holding said periphery immobile; and an electrically conductive flexible membrane disposed between said coil unit and said foil, said membrane being held between said coil unit and said foil with the perimeter of said membrane substantially mechanically unrestrained.

2. A shock wave source as claimed in claim 1, wherein said membrane consists of aluminum.

3. A shock wave source as claimed in claim 1, wherein said membrane has a thickness in the range of from about 50 μm to about 500 μm.

4. A shock wave source as claimed in claim 1, wherein said foil consists of a polymeric plastic.

5. A shock wave source as claimed in claim 1, wherein said foil consists of polyimide.

6. A shock wave source as claimed in claim 1, wherein said foil consists of polyethylene.

7. A shock wave source as claimed in claim 1, wherein said shock wave source further comprises a housing, wherein said means for holding said periphery is a part of said housing, and wherein said means for holding said periphery is a means for clamping said periphery of said foil in said housing.

8. A shock wave source as claimed in claim 7, wherein said housing consists of two separable housing components each having a planar surface between which said periphery of said foil is disposed, and wherein said means for holding is a fastener forcing said planar surfaces together to clamp said foil therebetween.

9. A shock wave source as claimed in claim 7, wherein said housing is cylindrical and has an inside diameter, and wherein said membrane has a diameter less than the inside diameter of said housing.

10. A shock wave source as claimed in claim 1, wherein said coil unit, said membrane and said foil are concave.

11. A shock wave source as claimed in claim 1, wherein said membrane has a central opening therein.

12. A shock wave source as claimed in claim 11, wherein said central opening has a diameter in the range of from about 10 to about 30% of the diameter of the membrane.

13. A shock wave source as claimed in claim 1, wherein said coil unit, said foil and said means for folding said periphery define a volume, and further comprising means for generating a vacuum in said volume.

14. A shock wave source as claimed in claim 1, wherein said foil is reinforced at said periphery thereof.

15. A shock wave source as claimed in claim 1, wherein said coil unit comprises a helical coil cast in casting resin.

16. A shock wave source comprising:

a high voltage pulse supply;

means adapted for connection to said high voltage power supply for generating an electromagnetic field in response to a pulse from said supply;

flexible electrically conductive means disposed adjacent said means for generating an electromagnetic field for rapidly moving away from said means for generating an electromagnetic field in response to the electromagnetic field generated thereby, said electrically conductive means having a perimeter;

flexible electrically non-conductive means disposed adjacent said electrically conductive means for mechanically interacting with said electrically conductive means as said electrically conductive means moves in response to said electromagnetic field; and means for holding said electrically non-conductive means at a periphery thereof against said means for generating an electromagnetic field with said electrically conductive means therebetween with the perimeter of said electrically conductive means substantially mechanically unrestrained.

17. A shock wave source as claimed in claim 16, wherein said means for generating an electromagnetic field is a helical coil cast in insulating resin.

18. A shock wave source as claimed in claim 16, wherein said electrically conductive means in an aluminum membrane.

19. A shock wave source as claimed in claim 16, wherein said electrically non-conductive means is a polymeric plastic foil.

20. A shock wave system comprising:

a high voltage pulse supply;

an electrically conductive coil unit and connection means adapted for connecting said coil unit to said high-voltage power supply, said coil unit having a central opening therein;

a flexible foil consisting of material having poor electrical conductivity;

means for securing said foil against said coil unit at the periphery of said foil;

an electrically conductive flexible membrane disposed between said coil unit and said foil, said membrane being held between said coil unit and said foil with the perimeter of said membrane substantially mechanically unrestrained, said membrane having a central opening therein in registry with said central opening in said coil unit; and means for ultrasonic locating of objects disposed in said respective central openings in said coil unit and said membrane.

* * * * *